United States Patent [19]

Yamashita

[11] Patent Number: 4,625,572

[45] Date of Patent: Dec. 2, 1986

[54] CYLINDER PUMP

[75] Inventor: Kiyoshi Yamashita, Ootawara, Japan

[73] Assignee: Kabushiki Kaisha Toshiba, Japan

[21] Appl. No.: 724,153

[22] Filed: Apr. 17, 1985

[30] Foreign Application Priority Data

Apr. 18, 1984 [JP] Japan .................... 59-79039

[51] Int. Cl.⁴ ............................................. G01N 1/14
[52] U.S. Cl. .................................... 73/864.16; 92/170
[58] Field of Search ............... 73/864.16; 604/187; 92/170

[56] References Cited

U.S. PATENT DOCUMENTS 2,607,342 8/1952 Abel ............................... 92/170 X
4,315,454 2/1982 Knodel ............................. 92/170
4,516,479 5/1985 Vadasz ............................. 92/170

FOREIGN PATENT DOCUMENTS 2541642 3/1977 Fed. Rep. of Germany .
372526 10/1983 Fed. Rep. of Germany .
1569984 6/1980 United Kingdom .

Primary Examiner—Jerry W. Myracle
Attorney, Agent, or Firm—Finnegan, Henderson, Farabow, Garrett & Dunner

[57] ABSTRACT

The invention provides a cylinder pump for an automatic chemical analyzer or the like, which comprises a cylinder and a plunger both made of a rigid material and coupled together in a liquid-tight sliding contact with each other without any elastic member such as an O-ring interposed between the sliding contact surfaces, whereby to constitute a pump mechanism for withdrawing and discharging liquid, the sliding contact surfaces being mirror-like surface. Ceramics are used as the rigid material of the cylinder and plunger. Hence, the cylinder pump has high discharge accuracy, long life and improved measurement precision.

4 Claims, 7 Drawing Figures

CYLINDER PUMP

BACKGROUND OF THE INVENTION

This invention relates to a cylinder pump used for automatic chemical analyzers or the like.

The automatic chemical analyzer is an apparatus which can automatically analyze a sample for biochemical inspection thereof. Particularly, it is used to analyze a number of test specimens quickly and accurately for a wide variety of inspection items. FIG. 5 illustrates a typical analyzer of this type. The analyzer comprises sampling pumps 1, distributing nozzles 2 coupled to the sampling pumps 1 through tubes, a number of serum samples 3, a reaction trough 4 with a number of reaction cells 4a accommodating the test specimens, a nozzle 5 for charging a reagent into the reaction cells, an optical measuring section 6 including light sources 6a, reflecting mirrors 6b and light-receiving sections 6c, and a control section 7 including an operation panel 7a, a CPU 7b and an operational section 7c. The sampling pumps 1, distributing nozzles 2, reagent charging nozzle 5 and optical measuring section 6 are driven under the control of the control section 7. Data representing the quantity, number, position, etc. of serum samples is input from the operation panel 7a to the CPU 7b. The total quantity of serum withdrawn by the distributing nozzles 2 is calculated by the CPU 7b and operational section 7c, and the CPU 7b produces a signal showing the calculated quantity of serum. According to this signal, a driver for the sampling pumps 1, which includes a pulse motor 1a, a lead screw 1b and a plunger retainer 1c, is driven, whereby a predetermined quantity of serum samples 3 is sucked in through the distributing nozzles 2. The nozzles 2 are then moved to a predetermined discharge position in the reaction trough 4 and discharge the serum into corresponding reaction cells 4a. A reagent X is poured through the reagent charging nozzle 5 into the reaction cells, and the resultant mixture is agitated to cause reaction. The mixture is transferred to the optical measuring section 6 for optical analysis with respect to an intended inspection item.

The sampling pump for the automatic chemical analyzer as described above is a cylinder pump as shown in FIG. 1. The cylinder pump comprises a cylindrical holder 10 and a cylindrical glass cylinder 11 fitted in the holder 10. In the glass cylinder 11 is slidably inserted a plunger 13 with O-rings 12 of an elastic material used as seal members. The holder 10 has a cap 14 fitted at the end, and liquid is withdrawn and discharged through a hole 14a in the cap 14. In this prior art cylinder pump, the O-rings 12 are deformed randomly as they slide in frictional contact with the galss cylinder 11 when the plunger 13 operates. The deformation of the O-rings 12 results in subtle changes in the quantity of the liquid withdrawn or discharged. In addition, the frictional resistance of the O-rings 12 is not the same at all time. Therefore, where the plunger 13 is driven by, for example, a pulse motor, the motor is not stopped at a given rotational position because the frictional resistance per se of the O-ring is not always constant and the accuracy with which the liquid is withdrawn and discharged is impaired. The chemical analyzer, where a multi-ganged cylinder pump is driven by a single motor, cannot accurately analyze samples since the quantities of the liquid withdrawn or discharge inevitably changes.

Further, the O-rings which are made of an elastic material are worn out during repetitive use. The flakes portions of worn-out O-rings get into a flow path of the apparatus, clogging electromagnetic valves, check valves, nozzles, etc. to cause operation errors. This also deteriorates the accuracy of measurement.

SUMMARY OF THE INVENTION

Accordingly, the object of this invention is to provide a cylinder pump which has high discharge accuracy and long life and can contribute to the improvement of the measurement precision.

According to the invention, there is provided a cylinder pump for an automatic chemical analyzer or the like, which comprises a cylinder and a plunger both made of a rigid material and coupled together in a liquid-tight sliding contact with each other without any elastic member such as an O-ring interposed between the sliding contact surfaces, whereby to constitute a pump mechanism for withdrawing and discharging liquid, the sliding contact surfaces being mirror-like surface. Ceramics are used as the rigid material of the cylinder and plunger. Hence, the cylinder pump has high discharge accuracy, long life and improved measurement precision.

DETAIL DESCRIPTION OF THE PREFERRED EMBODIMENTS

Figure 1:
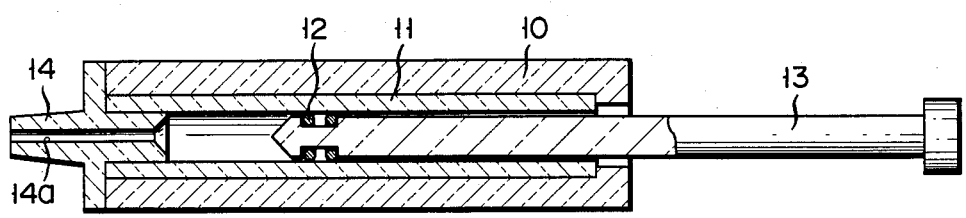
FIG. 1 is a sectional view of the conventional cylinder pump.
Figure 2:
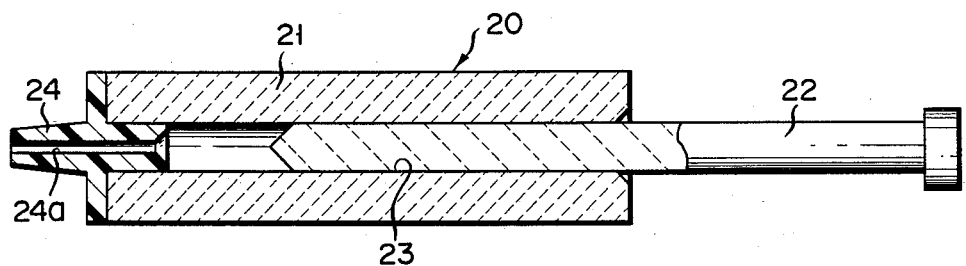
FIG. 2 is a sectional view of an embodiment of the cylinder pump according to the invention.

Referring to FIG. 2, there is shown an embodiment of the cylinder pump 20, in which both the cylinder 21 and plunger 22 are made of the same rigid material and are in liquid-tight sliding contact with each other. Their sliding contact surface 22 is formed to have a mirror surface, for instance with a surface roughness of about 3 $\mu$m or below. The cylinder 21 has a cap 24 provided at one end and having a hole 24a communicating with the cylinder interior.

The rigid material of the cylinder and plunger should not undergo physical deformation such as flexing under a load. In addition, the cylinder should be made of such a rigid material as to have a liquid-tight property and wear resistance. Otherwise, the cylinder and plunger cannot constitute a cylinder pump unless an elastic sliding member such as an O-ring is interposed between their contact surfaces. Thus, a mere rigid material, such as glass, having such a mere property as to produce no physical deformation, such as flexing, under a lood is not suitable in accordance with this invention. That is, if the cylinder and plunger are both made of glass, silicon is precipitated at their sliding contact surfaces due to a repetitive use, adversely affecting the liquid-tightness and slidability. This is prominently so if both the contact surfaces are made mirror-like. In order to avoid such a problem, a ceramic material in particular is most suited. A suitable ceramic material is of alumina type or zirconia type. The ceramic material of zirconia type may be those which contain 0.0053% of $Na_2O$, 0.0026% of $K_2O$, 0.0087% of MgO and 0.0048% of CaO.

Since the cylinder and plunger are made of the same rigid material and are in liquid-tight sliding contact, the plunger operation is performed, owing to the uniform frictional resistance offered by the rigid sliding contact surfaces. Thus, unlike in the conventional cylinder pump using an intervening elastic sliding member, the quantity of withdrawn or discharged liquid will never fluctuate.

Further, since the cylinder pump is hardly worn even in long use, there is no possibility for any piece or flake such as portions of worn-out elastic O-rings to get into the flow path to adversely affect other sections of the apparatus. Thus, it is possible to provide a cylinder pump having a very stable and highly accurate performance. Further, the mirror-like surface sliding contact surfaces of the cylinder and plunger have very low frictional resistance and also have liquid-tightness. Thus, the plunger pump has excellent discharge accuracy and operability and also has wear resistance.

Figure 5:
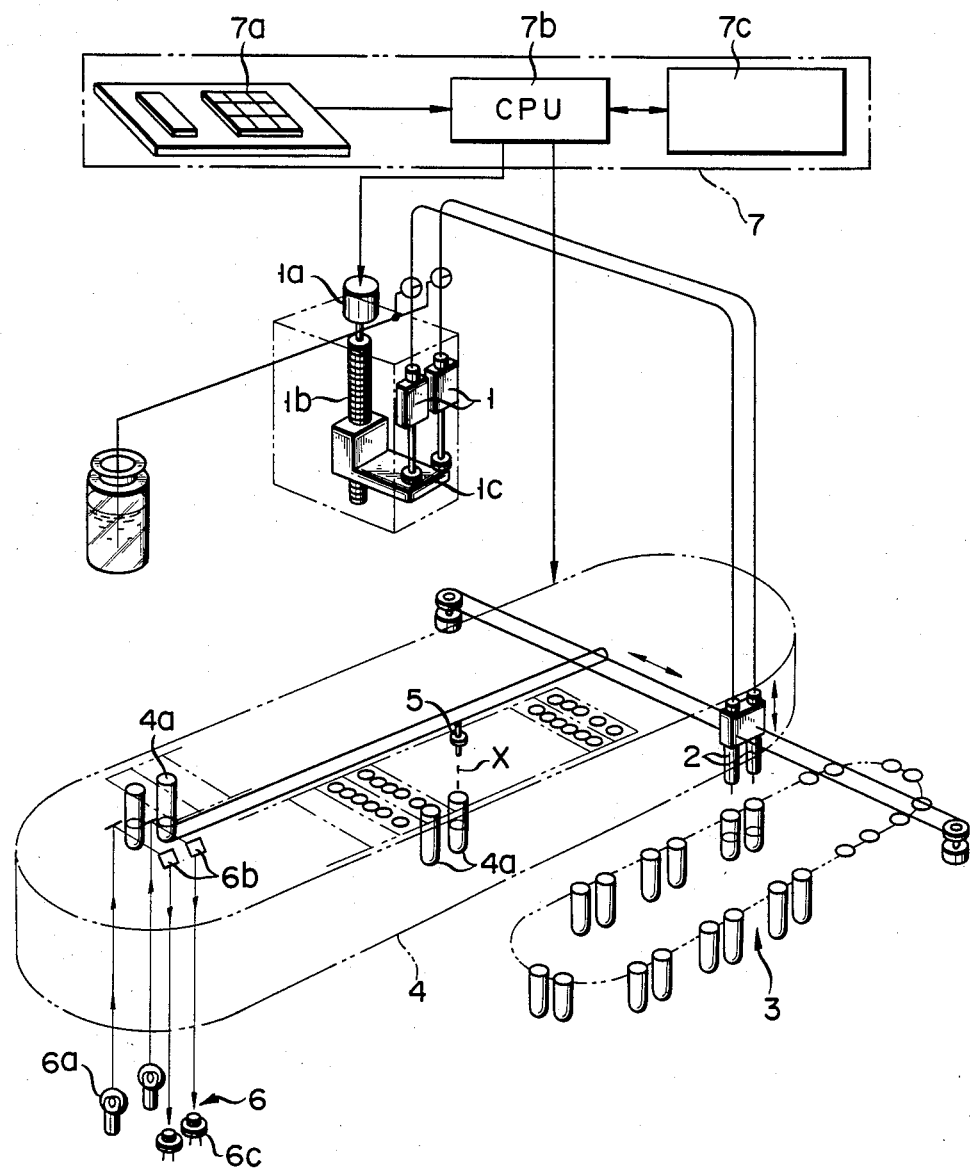
FIG. 5 is a schematic view of an automatic chemical analyzer employing cylinder pumps as sampling pumps.

When the cylinder pump 20 as described above according to the invention is employed as the sampling pumps 1 in the automatic chemical analyzer shown in FIG. 5, a predetermined quantity of serum sample corresponding to the displacement of the plunger 22 moving in the cylinder 21, i.e., the volume of the space formed in the cylinder 21, is withdrawn by each distributing nozzle 2, and also a predetermined quantity of serum sample corresponding to the plunger displacement is discharged from each distributing nozzle 2 into each reaction cells 4a. The difference in the discharge quantity from the individual distributing nozzles is very small, and the accuracy is extremely improved over the prior art cylinder pump.

Figure 3:
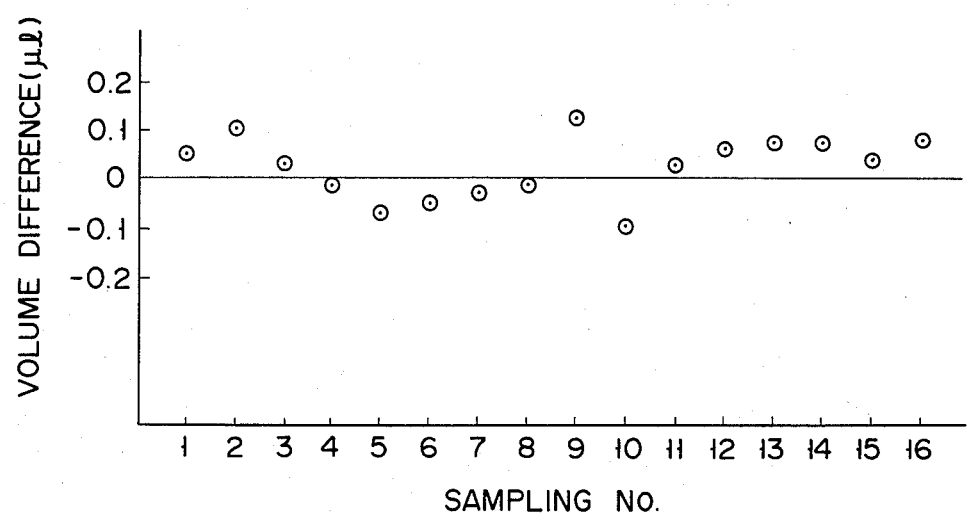
FIG. 3 is a graph showing the volume difference of the quantity of liquid discharge of the prior art cylinder pump.
Figure 4:
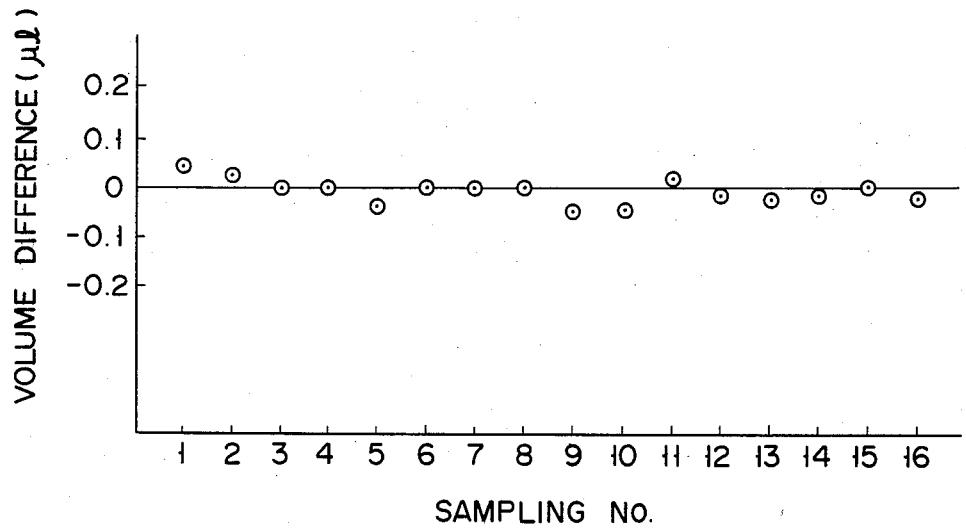
FIG. 4 is a graph showing the volume difference of the quantity of liquid discharged by the cylinder pump shown in FIG. 2.

FIG. 3 is a graph showing the fluctuations, i.e., volume difference, of the discharge quantity when 5 $\mu$l of liquid was poured into a plurality (i.e., No. 1–No. 16) of reaction cells 4a in the reaction trough 4 using two prior art cylinder pumps as the sampling pumps. As is seen from the Figure, there are great fluctuations both in the positive and negative direction on the zero volume difference line, indicating a great difference in the discharge quantity from the individual cylinder pumps.

FIG. 3 shows the volume difference of the discharge quantity observed when the cylinder pumps of the above embodiment are used as sampling pumps in the apparatus shown in FIG. 5. In this case, positive and negative fluctuations on the zero volume difference line are very small, indicating that a difference of the discharge quantity from the individual cylinder pumps are very slight. The cylinder pump according to the invention thus ensures for higher accuracy than the prior ar cylinder pump.

The embodiment of the cylinder pump described above is by no means limitative, and its construction can be variously modified within the scope of the invention.

Figure 6:
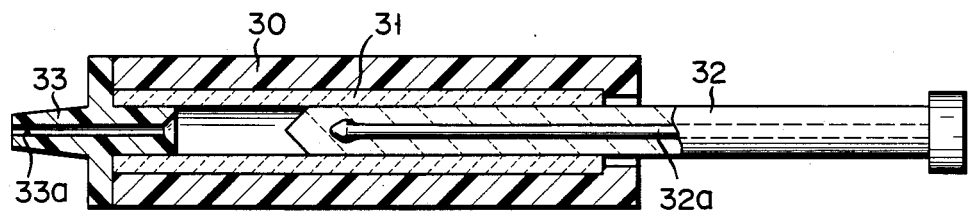
FIG. 6 is a sectional view showing a modification of the cylinder pump shown in FIG. 2.

For example, the above embodiment of the cylinder pump may be accommodated in a holder, i.e., a cylindrical holder made of a suitable rigid material such as hard synthetic resins or metals and having a cap provided at one end and having a hole. In this case, the cylinder wall may be thinner than in the above embodiment, while obtaining the same function and effects. The reinforcement structure is also applicable to the plunger. FIG. 6 shows a modification of the above embodiment where the cylinder is reinforced.

This cylinder pump comprises a holder 30, a cylinder 31, a plunger 32 reinforced with a metal rod 32a and a cap 33 with a hole 33a. The cylinder 31 and outer layer of the plunger 32 are made of ceramic material. The plunger outer layer is formed by sintered ceramic powder. The ceramic outer layer of the plunger 32 reinforced with the center rod 32a is not required to have a mechanical strength required of, for example, the plunger in the above embodiment, which is an independent rigid member. Therefore, the layer may be thin, and it is only necessary to make its sliding contact surface co-operating with the cylinder inner wall have a mirror surface. By so doing, the same function and effects as with the above embodiment of the cylinder pump can be obtained.

Figure 7:
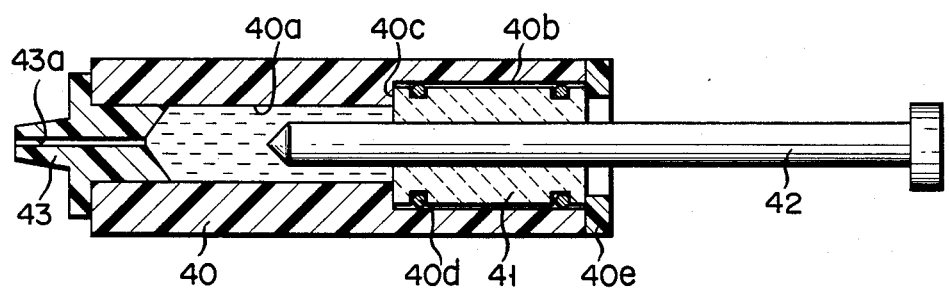
FIG. 7 is a sectional view showing a different embodiment of the cylinder pump according to the invention.

FIG. 7 shows another embodiment of the invention, i.e., a cylinder pump of holder type. This pump comprises a cylinder holder 40 made of a synthetic resin, a cylinder 41 and a plunger 42 both made of a ceramic material and having a mirror-like frictional contact surface, and a cap 43 mounted on the end of the holder 40. The holder 42 includes a cavity 40a communicating with the hole 43a in the cap 43 and which defines a liquid chamber and a circular recess 40b communicating with the cavity 40a at a shoulder 40c and in which the cylinder 41 is fittedly supported. As shown, the circular recess 40b has a diameter larger than that of the cavity 40a, which is so arranged that the plunger may extend forwardly therethrough with a clearance therearound. The cylinder 41 is elastically supported in the circular recess 40b with elastic members, e.g., O-rings 40d, fitted on its outer periphery. A cylinder retainer 40e is provided at the rear end of the holder 40.

Again with this cylinder pump, the cylinder 41 and plunger 42 have mirror-like sliding contact surfaces. A predetermined quantity of liquid can be withdrawn or discharged in accordance with a displacement of the cylinder 42 into or out of the cavity 40a. Therefore, the same function and effects as in the case of the previous embodiment can be obtained. Further, the plunger 42 is slidably inserted into the cylinder 41 and supported elastically through the O-rings 40d in the circular recess 40b of the holder 40 such that its end portion extends into the cavity 40a with a clearance therearound and the plunger is coaxial with the holder at all time. This provides an excellent operability when inserting and withdrawing the plunger. With the previous first embodiment of the cylinder pump where the entire length of the plunger is in sliding contact with the cylinder inner wall, a force exerted upon the plunger in a direction biased from the axial direction would immediately cause a fault operation of the plunger. Therefore, fine adjustment or careful inspection is always required for the use of the cylinder pump. With the present embodiment, the cylinder 41, which is located in a rear portion of the holder and elastically supported therein, can dampingly absorbs such a force exerted in a deviated axial direction to immediately restore the plunger to the exact coaxial position. Thus, the plunger can smoothly and readily operate, which is particularly desired for the automatic chemical analyzer which requires a finely and exactly controlled operation.

The cylinder pump having the function and effects as described above according to the invention, can be used not only as the sampling pump but also as various other pumps in the same apparatus for reagent charging, washing, drying, etc. In any of these applications, it can serve as a cylinder pump which has high accuracy, excellent operability and long life. Further, it can be used in the pump of this type or the like for other machines that the automatic chemical analyzer.

What is claimed is:

1. A cylinder pump for an automatic chemical analyzer or the like, comprising:
   a cylinder made of a ceramic material and having a mirror-like inner surface; and
   a solid plunger made substantially of the same ceramic material as that of said cylinder and having a mirror-like outer surface, said plunger being movable within said cylinder and said outer surface of said plunger being in liquid-tight sliding contact with said inner surface of said cylinder for precisely withdrawing and discharging a predetermined volume of liquid into and out of said cylinder.

2. The cylinder pump according to claim 1, further comprising a cylindrical holder supporting said cylinder therein, said cylindrical holder having at one end a nozzle including a hole portion communicating with the interior of said cylinder.

3. The cylinder pump according to claim 2, wherein:
   said cylindrical holder includes a forward liquid chamber adjacent said one end of said holder and a cylindrical recess adjacent the other end of said holder;
   said cylinder is elastically supported within said recess; and
   said plunger is extendable through said cylinder and into said forward liquid chamber.

4. The cylinder pump according to claim 1, wherein said plunger includes a metal reinforcing rod imbedded therein.

* * * * *